United States Patent [19]

Saiki et al.

[11] Patent Number: 5,283,379
[45] Date of Patent: Feb. 1, 1994

[54] METHOD FOR PRODUCING TRIFLUOROETHYLENE

[75] Inventors: Takao Saiki; Makoto Sumida; Satohiro Nakano, all of Shinnanyo; Kengo Murakami, Hofu, all of Japan

[73] Assignee: F. Tech, Inc., Tokyo, Japan

[21] Appl. No.: 47,009

[22] Filed: Apr. 15, 1993

Related U.S. Application Data

[63] Continuation of Ser. No. 737,656, Jul. 30, 1991, abandoned.

[30] Foreign Application Priority Data

Aug. 13, 1990 [JP]  Japan ................... 2-214113

[51] Int. Cl.⁵ .............................................. C07C 17/34
[52] U.S. Cl. ................................................... 570/156
[58] Field of Search ......................................... 570/156

[56] References Cited

U.S. PATENT DOCUMENTS 2,697,124 12/1954 Mantell ................. 570/156
4,876,405 10/1989 Gervasutti ............. 570/156

FOREIGN PATENT DOCUMENTS 655397 1/1963 Canada ................... 570/156

Primary Examiner—Alan Siegel
Attorney, Agent, or Firm—Oblon, Spivak, McClelland, Maier & Neustadt

[57] ABSTRACT

Method for producing TrFE by reaction of R-113 with hydrogen in the presence of a catalyst comprising palladium and at least one selected from gold, tellurium, antimony, bismuth, and arsenic, supported on an inert carrier. TrFE can be produced from R-113 and hydrogen through one-step reaction by use of the catalyst.

6 Claims, No Drawings

METHOD FOR PRODUCING TRIFLUOROETHYLENE

This application is a continuation of application Ser. No. 07/737,656, filed on Jul. 30, 1991, now abandoned.

BACKGROUND OF THE INVENTION

1. Field of the Invention

The present invention relates to an improved method for producing trifluoroethylene (hereinafter referred to as "TrFE") by reaction of 1,1,2-trichloro-1,2,2-trifluoroethane (hereinafter referred to as "R-113") with hydrogen.

More particularly, the present invention relates to a method for producing TrFE by reaction of R-113 with hydrogen in the presence of a catalyst comprising palladium and at least one selected from gold, tellurium, antimony, bismuth, and arsenic.

2. Description of the Related Art

Trifluoroethylene is a useful compound as a monomer for functional fluorine-containing polymers and as an intermediate material for biologically active compounds.

A known method for producing TrFE is a reaction of chlorotrifluoroethylene (hereinafter referred to as "CTFE") with hydrogen in the presence of palladium or platinum supported by an active carbon carrier or an alumina carrier (Japanese Patent Publication No. Sho 46-2324, Japanese Patent Application Laid-Open No. Sho 62-252736, and U.S. Pat. No. 2,802,887).

This method, which uses CTFE as a starting material, requires production of CTFE, for example by dechlorination of R-113 with zinc.

Accordingly, this method of TrFE production requires naturally two steps of reactions passing through CTFE as an intermediate, which is disadvantageous industrially.

Another method is disclosed in which TrFE is produced in one step of gas-phase reaction of R-113 with hydrogen in the presence of palladium catalyst supported by active carbon (Japanese Patent Publication Sho 43-8454).

This method is highly advantageous for industrial production of TrFE since the TrFE is produced from R-113 and hydrogen through a direct one-step reaction.

This method, however, is still unsatisfactory for industrial production of TrFE because of low catalyst activity and the short life thereof.

After comprehensive investigation to solve the above-mentioned disadvantages, the inventors of the present invention found a highly active and long-lived catalyst for production of TrFE from R-113 and hydrogen, and have accomplished the present invention.

SUMMARY OF THE INVENTION

An object of the present invention is to provide a novel method of producing TrFE by a gas-phase one-step reaction of R-113 with hydrogen.

Another object of the present invention is to provide a novel catalyst for the method for producing TrFE by the above-mentioned method.

According to an aspect of the present invention, there is provided a method for producing TrFE by reaction of R-113 with hydrogen in the presence of a catalyst comprising palladium (Pd), and at least one member selected from gold (Au), tellurium (Te), antimony (Sb), bismuth (Bi), and arsenic (As).

As the catalyst, a multi-component type catalyst is used which comprises Pd, and at least one member selected from Au, Te, Sb, Bi, and As. Particularly preferred catalysts are the Pd-Te type, and the Pd-As type.

According to another aspect of the present invention, there is provided a catalyst for TrFE production, comprising Pd, and at least one selected from Au, Te, Sb, Bi, and As as active catalyst components supported on an inert carrier.

DETAILED DESCRIPTION OF THE PREFERRED EMBODIMENT

In the present invention, the active catalyst components may be supported on a carrier inert to the reaction. The inert carriers known are exemplified by active carbon, alumina, and the like.

The method for depositing the catalyst components on the carrier is not specially limited. Any suitable method may be employed. For example, a usual impregnation method may be employed. An ion-exchange method may be employed for acid-treated active carbon. Impregnation methods are particularly suitable since the catalyst components can be made to be supported uniformly and simply on a carrier such as active carbon. In the impregnation methods usually, a chloride or a nitrate of respective metals is dissolved in a solvent such as hydrochloric acid, water or an organic solvent to prepare solutions of respective metals, and the resulting solutions are separately or simultaneously impregnated into the active carbon or the like.

The Pd which is essential as the active catalyst component is supported in an amount ranging from 0.1 to 5% by weight, preferably from 0.5 to 2% by weight based on the carrier. With the amount of less than 0.1% by weight, the catalyst activity is low. On the contrary, even if the amount is increased to more than 5% by weight, the catalyst activity will not be further improved.

In the present invention, high catalyst activity can be achieved and long life of the catalyst activity can be realized only by combining Pd with one or more of catalyst components of Au, Te, Sb, Bi and As. The amount of the active components to be supported along with the Pd is not limited, but is preferably in the range of from 0.01 to 10% by weight, more preferably from 0.1 to 2% by weight based on the carrier in most cases.

The resulting catalyst which has Pd and at least one of Au, Te, Sb, Bi and As may be activated before use, for example, by packing it in a reaction tube provided with an electric heater, drying it under a nitrogen stream, and then heating the catalyst layer under a hydrogen stream, in place of the nitrogen stream, at a temperature of 250° C. to 400° C. for 1 to 4 hours.

In the present invention, R-113 and hydrogen can be reacted by a usual one-step gas-phase reaction in the presence of the aforementioned multi-component catalyst prepared as above. In the reaction, the R-113 and hydrogen are fed to a reactor preferably at a mole ratio ($H_2$/R-113) of from 0.5 to 4, more preferably 1.5 to 2.5. At the mole ratio of lower than 0.5, the conversion ratio is low disadvantageously. At the mole ratio of higher than 4, excess hydrogen remains in the reaction product, and purge of the hydrogen accompanies TrFE disadvantageously to cause loss of the TrFE on purification of the TrFE.

The space velocity (hereinafter referred to as "SV") of the gases to be reacted depends on the reaction temperature. The reaction is preferably conducted at a temperature in the range of from 150° to 400° C. and at an SV in the range of from 50 to 600 hr$^{-1}$.

The resulting TrFE can be recovered by isolation and purification according to a conventional method such as distillation.

According to the method of the present invention, TrFE can be produced starting from R-113 and hydrogen through one-step reaction by use of a catalyst having high activity and long life. Therefore, the method is highly significant industrially.

The present invention is explained in more detail by reference to Examples without limiting the invention in any way.

In the Examples and Comparative Examples, the conversion and the selectivity are the values calculated with the calculation formulas below.

Conversion ratio of R-113 =

$$\frac{\text{Fed } R\text{-113 (mol)} - \text{Unreacted } R\text{-113 (mol)}}{\text{Fed } R\text{-113 (mol)}} \times 100 \, (\%)$$

$$\text{Selectivity} = \frac{\text{TrFE produced (mol)}}{\text{Entire product (mol)}} \times 100 \, (\%)$$

EXAMPLE 1 a) Preparation of Catalyst A

To 0.75 g of palladium dichloride, 50 ml of 0.1 N aqueous hydrochloric acid was added, and the mixture was heated to dissolve the palladium dichloride. Thereto 45 g of active carbon pellets (3 mm in diameter, 3 mm in height) were added. The mixture was evaporated to dryness on a water bath with agitation, and the resulting matter was further dried in a drier kept at 150° C. for 2 hours.

The dried active carbon pellets prepared above were added to a solution of 0.19 g of tellurium tetrachloride in 100 ml of 0.1 N aqueous hydrochloric acid. The mixture was evaporated to dryness on a water bath with agitation, and the resulting matter was dried in a drier kept at 150° C. for 2 hours, thereby Catalyst A being obtained.

The analysis of the metals in Catalyst A by atomic absorption spectroscopy showed that 1% by weight of palladium and 0.2% by weight of tellurium based on the carrier were supported on the active carbon.

b) Production of TrFE

A SUS-304 vertical tubular gas-phase reactor was used which was provided with a heater and was 16.7 mm in inside diameter and 700 mm in length. 50 ml of Catalyst A was packed at the center portion of the tubular reactor, and the catalyst was dried at 200° C. under nitrogen stream. Then the nitrogen stream was changed to a hydrogen stream at a hydrogen flow rate of 110 ml/min, the temperature was raised to 300° C., and the catalyst was kept in this state for 3 hours to activate the catalyst.

After the activation, with the hydrogen flow rate kept unchanged, the reaction temperature was brought to 250° C., and the reaction was started by feeding R-113 at a flow rate of 0.47 g/min. The reaction was conducted at SV: 200 hr$^{-1}$, and H$_2$/R-113=2 mol/mol.

The reaction product coming out from the bottom portion of the reactor was introduced to water-washing column to eliminate the by-product hydrochloric acid, and was dried by passing it through calcium chloride layer. The composition of the final product was analyzed by gas chromatographic analysis. The results of the reaction at 40 hours and at 100 hours after the start of the reaction are shown below.

TABLE 1

| Time from Start of Reaction | 40 hr | 100 hr |
| --- | --- | --- |
| Conversion of R-113 (%) | 98 | 98 |
| Selectivity for TrFE (%) | 53 | 54 |

COMPARATIVE EXAMPLE 1

The reaction was conducted in the same manner as in Example 1 except that tellurium was not used and palladium was supported on the carrier in an amount of 0.5% by weight (Catalyst B), 1% by weight (Catalyst C), and 2% by weight (Catalyst D). The results of the reaction at 40 hours after the start of the reaction are shown for respective catalyst in Table 2.

TABLE 2

|  | Conversion of R-113 | Selectivity for TrFE |
| --- | --- | --- |
| Catalyst B | 75% | 52% |
| Catalyst C | 84% | 55% |
| Catalyst D | 83% | 57% |

EXAMPLE 2

Catalysts below were prepared by using the above Catalyst C, namely the active carbon carrier having palladium supported thereon, prepared in Comparative

EXAMPLE 1

Catalyst E 0.22 g of arsenic trichloride was dissolved in 200 ml of ethanol. Thereto 45 g of Catalyst C was added. The ethanol in the mixture was evaporated off to dryness. The resulting matter was further dried in a drier kept at 150° C. for 2 hours. The analysis gave the result that 1% by weight of palladium and 0.2% by weight of arsenic were supported on the carrier.

Catalyst F 0.07 g of bismuth trichloride was dissolved in 200 ml of ethanol. Thereto 45 g of Catalyst C was added. Evaporation to dryness and subsequent drying were conducted in the same manner as for the above Catalyst E. The analysis gave the result that 1% by weight of palladium and 0.1% by weight of bismuth were supported on the carrier.

Catalyst G 0.17 g of antimony trichloride was dissolved in 200 ml of ethanol. Thereto 45 g of Catalyst C was added. Evaporation to dryness and subsequent drying were conducted in the same manner as for the above Catalyst E. The analysis gave the result that 1% by weight of palladium and 0.2% by weight of antimony were supported on the carrier.

Catalyst H 0.19 g of gold trichloride was dissolved in 200 ml of ethanol. Thereto 45 g of Catalyst C was added. Evaporation to dryness and subsequent drying were conducted in the same manner as for the above Catalyst E. The analysis gave the result that 1% by weight of palladium and 0.2% by weight of gold were supported on the carrier.

The reaction was conducted with Catalysts E to H and otherwise in the same manner as in Example 1. The results at 40 hours and 100 hours after the start of the reaction are shown in Table 3. The result with Catalyst A is also shown in Table 3. For comparison, the result with Catalyst C is also shown in Table 3.

TABLE 3

| Catalyst Employed | After 40 hours | | After 100 hours | | Change of Activity with Time (%) |
|---|---|---|---|---|---|
| | Conversion of R-113 (%) | Selectivity for TrFE (%) | Conversion of R-113 (%) | Selectivity for TrFE (%) | |
| A: 1 wt % PD, 0.2 wt % Te | 98 | 53 | 98 | 54 | 102 |
| E: 1 wt % PD, 0.2 wt % As | 100 | 66 | 99 | 65 | 98 |
| F: 1 wt % PD, 0.1 wt % Bi | 100 | 51 | 93 | 48 | 88 |
| G: 1 wt % PD, 0.2 wt % Sb | 98 | 46 | 94 | 47 | 98 |
| H: 1 wt % PD, 0.2 wt % Au | 80 | 51 | 82 | 51 | 103 |
| C: 1 wt % PD, — | 84 | 55 | 70 | 53 | 80 |

In the Table, "Change of Activity with Time" is:

$$\frac{(\text{Conversion of R-113}) \times (\text{Selectivity for TrFE}) \text{ after 100 hours}}{(\text{Conversion of R-113}) \times (\text{Selectivity for TrFE}) \text{ after 40 hours}} \times 100(\%)$$

EXAMPLE 3

A catalyst having 1% by weight of palladium and 0.25% by weight of tellurium supported was prepared according to the procedure of Example 1. The reaction was conducted in the same manner as in Example 1 except that the reaction temperature was changed. The results are shown in Table 4.

TABLE 4

| Reaction Temperature (°C.) | Conversion of R-113 (%) | Selectivity for TrFE (%) |
|---|---|---|
| 150 | 19 | 33 |
| 180 | 61 | 40 |
| 200 | 88 | 50 |
| 220 | 97 | 54 |
| 260 | 100 | 57 |
| 300 | 100 | 55 |

EXAMPLE 4

A catalyst having 1% by weight of palladium and 0.25% by weight of tellurium supported was prepared according to the procedure of Example 1. The reaction was conducted in the same manner as in Example 1 except that the reaction temperature was set to 260° C., and the mole ratio (H$_2$/R-113) was varied. The results are shown in Table 5.

TABLE 5

| Hydrogen/R-113 mole ratio | Conversion of R-113 (%) | Selectivity for TrFE (%) |
|---|---|---|
| 1.0 | 48 | 52 |
| 1.5 | 71 | 52 |
| 2.0 | 100 | 57 |
| 2.5 | 97 | 57 |

EXAMPLE 5

Catalyst I having palladium and tellurium supported respectively in amounts of 0.5% and 0.1% by weight, and Catalyst J having palladium and tellurium supported respectively in amounts of 2% and 0.4% by weight were prepared according to the method of Example 1. The reaction was conducted in the same manner as in Example 1. The results at 40 hours after the start of the reaction are shown in Table 6.

Further, Catalyst K having palladium and arsenic supported respectively in amounts of 0.5% and 0.1% by weight, Catalyst L having palladium and bismuth supported respectively in amount of 2% and 0.2% by weight, Catalyst M having palladium and antimony supported respectively in amounts of 0.5% and 0.1% by weight, and Catalyst N having palladium and gold supported respectively in amounts of 2% and 0.4% by weight were prepared, and the reaction was conducted according to the method of Example 2. The results at 40 hours after the start of the reaction are shown in Table 6.

TABLE 6

| Catalyst Employed | | Conversion of R-113 (%) | Selectivity for TrFE (%) |
|---|---|---|---|
| I: | 0.5 wt % Pd, 0.1 wt % Te | 88 | 51 |
| J: | 2 wt % Pd, 0.4 wt % Te | 99 | 52 |
| K: | 0.5 wt % Pd, 0.1 wt % As | 88 | 63 |
| L: | 2 wt % Pd, 0.2 wt % Bi | 100 | 51 |
| M: | 0.5 wt % Pd, 0.1 wt % Sb | 86 | 46 |
| N: | 2 wt % Pd, 0.4 wt % Au | 82 | 50 |

What is claimed is:

1. A method for producing trifluoroethylene by reaction of 1,1,2-trichloro-1,2,2-trifluoroethane with hydrogen in the presence of a catalyst comprising form 0.1 to 5% by weight of palladium and from 0.01 to 10% by weight of at least one member selected from the group consisting of gold, tellurium, antimony, bismuth, and arsenic supported on a carrier.

2. The method for producing trifluoroethylene according to claim 1, wherein the mole ratio of the hydrogen to 1,1,2-trichloro-1,2,2-trifluoroethane used in the reaction is in the range of from 0.5 to 4.0.

3. The method according to claim 1, wherein the amount of said supported Pd ranges from 0.5 to 2% by weight.

4. The method according to claim 1, wherein the amount of said at least on member ranges from 0.1 to 2% by weight.

5. The method according to claim 1, wherein the reaction is conducted at a temperature in the range of from 150° to 400° C. at a space velocity of reactants ranging from 50 to 600 hr$^{-1}$.

6. The method according to claim 2, wherein said ratio ranges from 1.5 to 2.5.

* * * * *